(12) United States Patent
Shermer et al.

(10) Patent No.: US 12,285,326 B2
(45) Date of Patent: Apr. 29, 2025

(54) TIPS STENT GRAFT AND KIT

(71) Applicant: Angiomed GmbH & Co. Medizintechnik KG, Karlsruhe (DE)

(72) Inventors: Charles D. Shermer, Raleigh, NC (US); Alexander Lastovich, Raleigh, NC (US); Sebastian Zickwolf, Karlsruhe (DE); Pia U. Braeuer, Königsbach-Stein (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 17/773,576

(22) PCT Filed: Oct. 30, 2019

(86) PCT No.: PCT/EP2019/079638
§ 371 (c)(1),
(2) Date: Apr. 29, 2022

(87) PCT Pub. No.: WO2021/083505
PCT Pub. Date: May 6, 2021

(65) Prior Publication Data
US 2022/0346935 A1    Nov. 3, 2022

(51) Int. Cl.
*A61F 2/07* (2013.01)
*A61F 2/958* (2013.01)
*A61B 18/00* (2006.01)
*A61B 18/14* (2006.01)

(52) U.S. Cl.
CPC .............. *A61F 2/07* (2013.01); *A61F 2/958* (2013.01); *A61B 2018/0022* (2013.01); *A61B 18/14* (2013.01); *A61F 2210/0023* (2013.01); *A61F 2250/001* (2013.01)

(58) Field of Classification Search
CPC ........ A61F 2/06; A61F 2250/001; A61F 2/07; A61F 2/958; A61F 2210/0023; A61M 27/002; A61L 31/14
See application file for complete search history.

(56) References Cited

U.S. PATENT DOCUMENTS

| 6,077,298 A | 6/2000 | Tu et al. |
| 6,120,534 A | 9/2000 | Ruiz |
| 6,315,708 B1 * | 11/2001 | Salmon ............... A61F 2/958 |
| | | 600/3 |

(Continued)

FOREIGN PATENT DOCUMENTS

| WO | 94/01056 A1 | 1/1994 |
| WO | 03028522 A2 | 4/2003 |
| WO | WO-2007107327 A1 * | 9/2007 ............ A61M 25/10 |

OTHER PUBLICATIONS

PCT/EP2019/079638 filed Oct. 30, 2019 International Preliminary Report on Patentability dated Sep. 22, 2020.

*Primary Examiner* — Brian E Pellegrino
(74) *Attorney, Agent, or Firm* — Rutan & Tucker LLP

(57) ABSTRACT

The present invention relates to a TIPS stent graft, comprising a tubular component having a lumen extending therethrough, the tubular component comprising a balloon expandable central section and a first and a second self-expanding section, the first and the second self-expanding section sandwiching the central section, the lumen extending through the first, central, and second sections, the stent graft being capable of selectively constricting the central section.

9 Claims, 2 Drawing Sheets

(56) References Cited

U.S. PATENT DOCUMENTS

| | | |
|---|---|---|
| 2004/0092892 A1 | 5/2004 | Kagan et al. |
| 2007/0142907 A1* | 6/2007 | Moaddeb .............. A61F 2/2418 623/1.18 |
| 2008/0194905 A1 | 8/2008 | Walsh |

* cited by examiner

TIPS STENT GRAFT AND KIT

PRIORITY

This application is a U.S. national stage application of International Application No. PCT/EP2019/079638, filed Oct. 30, 2019, which is incorporated by reference in its entirety into this application.

TECHNICAL FIELD

The present invention relates to stent grafts for use as transjugular intrahepatic portosystemic shunts (TIPS) and a kit comprising a TIPS stent graft.

TECHNICAL BACKGROUND

Portal hypertension is an increase in the pressure in the digestive organ venous vasculature system that is returning venous blood through the liver and eventually to the heart but which is obstructed due to a diseased liver condition (such as a liver cirrhosis).

A transjugular intrahepatic portosystemic shunt (TIPS) is used to address portal hypertension and its complications. The shunt which is made of a TIPS stent graft, i.e., a covered stent, re-roots venous blood from the portal vein to the hepatic vein to reduce the pressure gradient across the liver. However, post TIPS placement, 20% to 30% of the patients suffer hepatic encephalopathy due to an overly high venous flow bypassing the liver through the shunt. This is because a smaller proportion of the blood is filtered due to a large amount of blood bypassing the liver, so that a high volume of unfiltered blood and toxic molecules enters the brain. The thus caused hepatic encephalopathy goes along with neuropsychiatric abnormalities characterised by personality changes, intellectual impairment, and a depressed level of consciousness.

Further, there is a poor patient survival. The occurrence of hepatic encephalopathy leads to hospitalisation and is associated with a survival probability of about 42% over one year and 23% over 3 years. Given that hepatic encephalopathy is caused by the blood flow through the TIPS being excessively high, a need exists for a TIPS which can be reduced in its diameter post-placement.

On the other hand, it is also sometimes necessary to increase the diameter of the TIPS shunt post placement if not enough blood bypasses the liver and if thus, portal hypertension is not adequately treated.

Commercially available TIPS stent grafts have the ability to be adjusted from an initial diameter of about 8 mm to a diameter of about 10 mm to optimise the portal pressure at the time of placement. However, not all devices have the ability to be adjusted in their diameter after placement and, in particular, cannot be restricted in their diameter.

Accordingly, there is a need to provide a TIPS stent graft which can be increased in its diameter post-placement and which is capable of treating or avoiding hepatic encephalopathy.

SUMMARY OF THE INVENTION

The present invention has been performed in view of the above-mentioned considerations and aims at solving the issues mentioned previously.

The invention is defined by the TIPS stent graft according to claim 1. Preferred embodiments are defined in the dependent claims.

The invention relates to a TIPS stent graft. Such a stent graft is a covered stent which, typically, has uncovered ends formed by the bare stent underlying the stent graft at one longitudinal end for anchoring it within a patient's portal vein.

The TIPS stent graft comprises a tubular component which has a lumen extending therethrough. This lumen allows for blood to flow from one longitudinal end of the TIPS stent graft to the respective other longitudinal end.

That tubular component comprises a balloon expandable central section and a first and a second self-expanding section. The first and the second self-expanding sections sandwich the central section—i.e., when moving along the longitudinal axis of the stent graft, one has first a self-expanding section, then the balloon expandable section and then arrives at the respective other self-expanding section. By a self-expanding section, it is meant that this section will, when exposed to a patient's blood, be brought to body temperature (i.e. about 37° C.) and thus expand without having to be forcefully expanded by means of, for example, a balloon which is inflated. In contrast with this, the balloon expandable central section does not have that capability and will not be brought to an expanded configuration just by means of being brought to body temperature. As a balloon for inflating the central section, a percutaneous transluminal angioplasty (PTA) balloon is being considered.

The stent graft is arranged so as to selectively and reversibly reduce its cross-sectional diameter by restricting its central section. That is, there is provided a means to selectively cause the central section to have a narrower diameter. That is, the stent graft comprises a means which can be used to restrict the central section to thereby reduce the cross-sectional area of the stent graft which is available for blood flow. Accordingly, the stent graft according to the present invention can avoid or treat hepatic encephalopathy by means of having its cross-sectional area restricted. This will reduce the amount of blood flowing through the TIPS stent graft, which, in turn, will increase the amount of blood flowing through the liver. Since that blood will be filtered by the liver, the amount of unfiltered blood and toxic components reaching the brain is decreased, so that hepatic encephalopathy will be avoided or ameliorated.

With the inventive TIPS stent graft, it is preferably possible to expand the central section of the stent graft by placing, for example, a balloon catheter inside the central section and by then expanding the stent graft (via the balloon catheter or via some other means). This then allows for a bi-directional adjustability (i.e., that one can, if desired, expand and contract the TIPS stent graft), which can be done as often as needed to adjust the differential pressure or flow rate across the stent graft.

It is preferred if the central section comprising a shape memory alloy having a transition temperature above body temperature, the central section being configured to assume a configuration which is more constricted than the first and second sections in their expanded state when heated above its transition temperature. For example, one could use, as the stent for use in the stent graft of the present invention, a stent where the central section has a higher transition temperature than the adjacent portion. Accordingly, one could, with a very simple design, provide a TIPS stent graft which is bidirectionally adjustable in its diameter. The TIPS stent graft would then assume the narrower configuration when the central section is heated up sufficiently high. It is preferred that the transition temperature of the central section is so that heating the central section to that temperature for a short period of time does not cause injury to a patient.

A realistic temperature would preferably be greater than or equal to 45° C. and more preferably be between 45° C. and 60° C. Having a temperature of ~60° C. for a short period of time does not cause undue stress to the patient's body. It is possible to heat up the central section by means of introducing a catheter, for example an ablation catheter, into the central section and then heating up that catheter. Such a method appears most practical and easy to implement.

Alternatively or additionally, it is preferred if there is a separate constriction means for constricting the central section. By having such a separate means, one can use a much simpler stent design, since one does not have to incorporate the constriction capability into the stent itself.

It is preferred if the constriction means is a collar wrapped around the central section. The collar is arranged to selectively reduce its inner diameter to thereby constrict the central section. By having a collar which is wrapped around the central section, the constriction occurs over the whole circumference of the central section, compared with a situation where only parts of the circumference are restricted. This avoids non-uniformities in the constricted area.

It is preferred that the collar is arranged to selectively reduce its inner diameter upon application of heat. It is comparatively easy to apply heat to an implanted stent graft, for example by heating it up using induction heating (e.g. by means of an MRI device) or by leading a current through it. In both cases, the current losses inside the collar will heat up the collar, which will, in turn, restrict the central section. Once the collar cools back down to body temperature, it stays in the constricted configuration. It is also possible to active the collar by means of an application of a transient thermal pulse (for example by a heated catheter with is introduced into the stent graft). Such a collar can be comparatively easily activated.

It is also preferred that the collar comprises a metal. It is easy to heat up such a metal by means of conducting electricity through it or by induction heating.

It is also preferred that the collar is arranged to heat up upon application of electric energy to thus reduce its inner diameter. I.e., it will, due to the resistance of the material the collar is made of or comprises, heat up. This heating up will then cause the collar to shrink which will reduce the cross-sectional area of the stent graft. In order to supply electric energy, the stent graft comprises two or more electrodes to supply energy to the collar. By providing such electrodes, supplying energy is comparatively easy.

In that context, it is preferred that the electrodes are formed on an inside of the stent graft. With such a stent graft, one can, subsequent to implanting the stent graft, introduce a catheter having electrodes on its outside and bring those electrodes in contact with the electrodes of the stent graft. One can then supply energy to the stent graft through the catheter and thereby cause the stent graft to become constricted.

In that context, it is further preferred that the electrodes comprise first and second electrodes. The first electrodes are provided on the first self-expanding section whilst the second electrodes is provided on the second self-expanding section. With such an arrangement, the first and the second electrodes are spaced apart from one another since they are separated by the central section. This makes it easier to bring a catheter into contact with them, compared with a situation where they are more closely spaced.

It is preferred if the collar is formed as a cylinder. A cylinder provides a uniform and essentially non-varying force when constricted.

An alternative preferred method is to use a coil as the collar. Such a coil can be easily manufactured since it can be simply made from a wire wrapped around the central section.

It is also preferred that the collar comprises a shape memory alloy. Such shape memory alloys undergo a shape change when heated above a certain transition temperature, where that shape change can be chosen so as to constrict the central section of the stent graft. The shape change of such shape memory alloys (e.g. Nitinol) is well characterised. Thus, the resulting change in diameter is very predictable.

It is preferred that the shape memory alloy has a higher transition temperature than the first and the second sections (which are also typically made comprising shape memory alloys to achieve their self-expanding capability). In that way, when the stent graft is implanted in the body, the first and second sections will naturally expand and therefore position the stent graft in the body. However, the collar will not necessarily undergo such a transition since it has a higher transition temperature. In that respect, it is preferred that the transition temperature of the shape memory alloy of the collar is higher than body temperature but is not so high so as to cause significant damage to the body when heated to that temperature for a short period of time (for example, more than 45° C. or preferably between 45° C. and 60° C.). By heating the stent to that temperature, one can, when desired, constrict it but will not accidentally do so when implanting it in the body.

Another aspect of the present invention is a kit comprising the tips stent graft as defined in one of claims 7 to 9, together with a catheter arranged for supplying electric energy to the electrodes from the outside of the stent graft, for example from a power source external to the patient's body. In that way, one can place the catheter inside the implanted stent graft and can then cause it to become constricted.

DETAILED DESCRIPTION OF THE DRAWINGS

Figure 1:
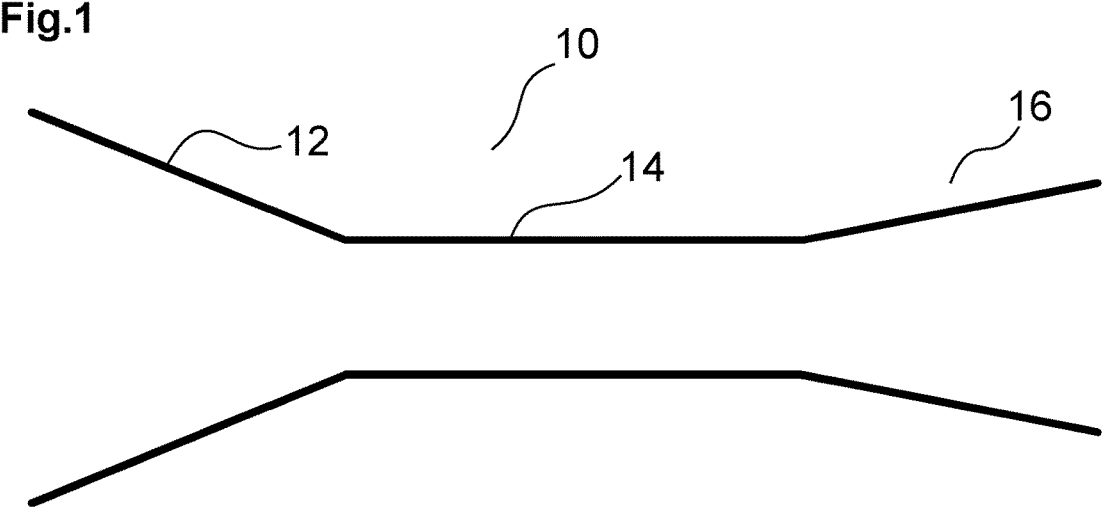
FIG. 1 shows a TIPS stent graft according to a first embodiment of the invention.

FIG. 1 shows, schematically, the configuration of a TIPS stent graft according to a first embodiment of the invention. The stent graft 10 comprises a first self-expanding section 12 made of bare nitinol. This section 12 can be placed inside the portal vein of a patient and is configured so that it will be at its programmed size at temperatures higher than 20° C.

Central section 14 is an ePTFE covered nitinol section that has a transition temperature of higher than 37° C. (for example 50° C.). This section has a programmed small nominal diameter of 6 mm or less at body temperature. At that temperature, the material of the stent used in the central section 14 is (at least mostly) in the martensitic state. In that configuration, it is malleable without being permanently set. If this central section 14 is raised to a higher temperature then its transition temperature, it will return to its original small diameter.

Second section 16 is an ePTFE covered self-expanding nitinol section that is at a programmed size at temperatures larger than 20° C., for example at body temperature. Thus, at body temperature, it expands to the larger diameter.

When placing the stent graft 10 in the liver channel which has been created for the TIPS procedure, first and second sections 12 and 16 expand to their programmed full diameter. In the case of first self-expanding section 12, this helps in locating the stent graft and anchoring it in the portal vein. In the case of section 16, this helps in ensuring that there is no flow restriction in that section whilst also potentially helping with locating it and anchoring it.

The physician would then use a balloon to open up the central section 14 to its intended diameter (typically 8-10 mm). This would be larger than its nominal diameter of 6 mm or less. The material would stay in this expanded shape without being damaged as long as the liver tissue does not collapse the stent. If in that configuration, the pressure balance is acceptable, no further steps are necessary.

Should the physician later need to reduce the flow through the stent graft 10 (due to hepatic encephalitis or for other reasons), he needs to only raise the temperature of the central section 14 above the transition temperature. This may be accomplished by inserting a heater via a catheter, by applying a voltage to the stent or by any other method such as, for example, induction heating to raise the local temperature to, for example, 50° C. for a short period. It may also be possible to do this using an MRI device or some other method which heats up the stent graft noninvasively.

When the temperature of the stent is raised above the transition temperature of the central section 14, the material of the central section 14 will be reset to its pre-programmed small diameter, which will reduce the flow through the stent graft 10. If the thus achieved default setting of the cross-sectional diameter of the stent graft 10 is acceptable, no further action is required. On the other hand, if the physician needs to reopen the central section 14 to a larger diameter, he could do this by letting the central section 14 cool down to body temperature and by re-expanding it with a balloon to its desired size.

This would, effectively, allow for the placement of a 9 or 10 mm diameter stent graft in the first instance. If the stent is too big, it can be reset to 6 mm or smaller and then resized to 7 or 8 mm. This procedure could be repeated as many times as necessary to set the correct diameter.

Since central section 14 would be covered with ePTFE or other suitable materials, the covering would to prevent bile or other fluids from the liver from entering the bloodstream. This also means that surrounding tissue would not crawl into the stent graft 10, so the change in diameter when expanding or constricting the stent graft 10 should not cause damage to the surrounding liver tissue even after several weeks or months of implantation.

Figure 2:
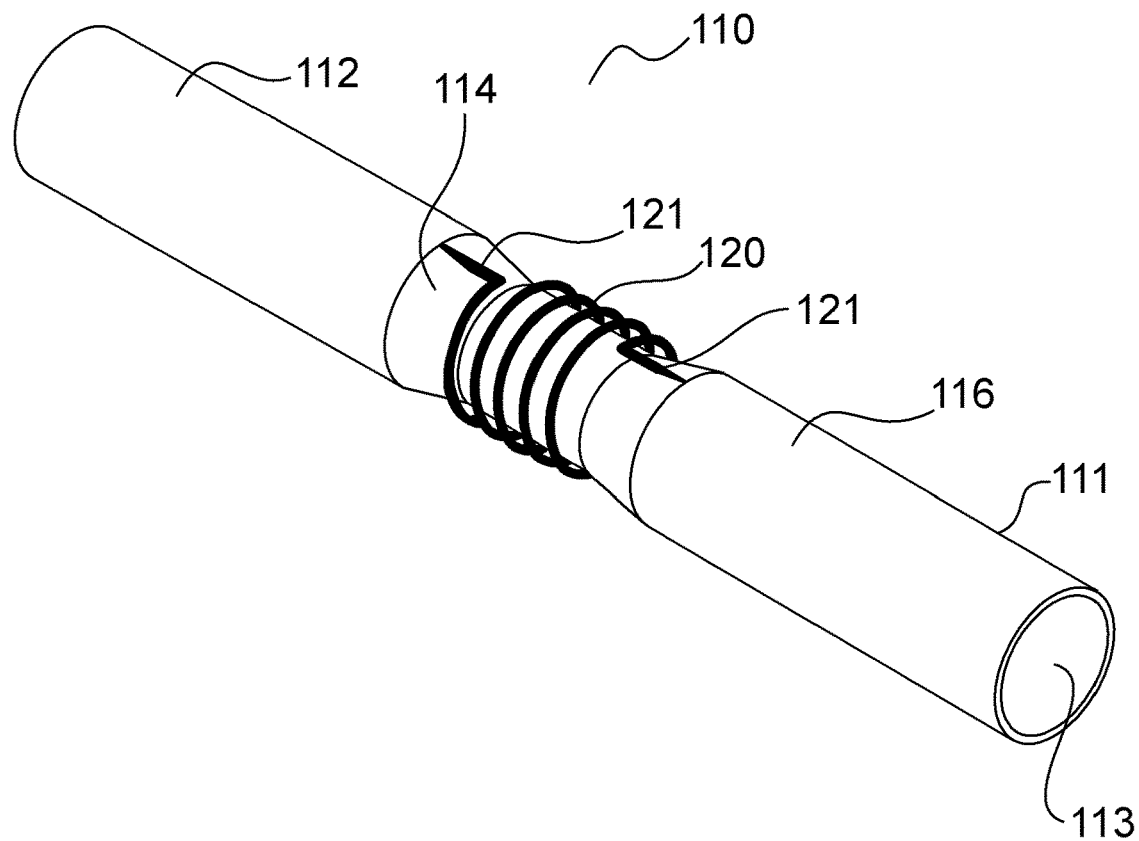
FIG. 2 shows a TIPS stent graft according to a second embodiment of the invention.

FIG. 2 shows a more detailed view of a second embodiment of the present invention. A stent graft 110 comprises a first self-expanding section 112 and a second self-expanding section 116. Together with the central section 114, they constitute the tubular component 111 of the TIPS stent graft 110. As can be seen from the drawing, a lumen 113 extends through the stent graft 110 from one end to the respective other end.

Figure 3:
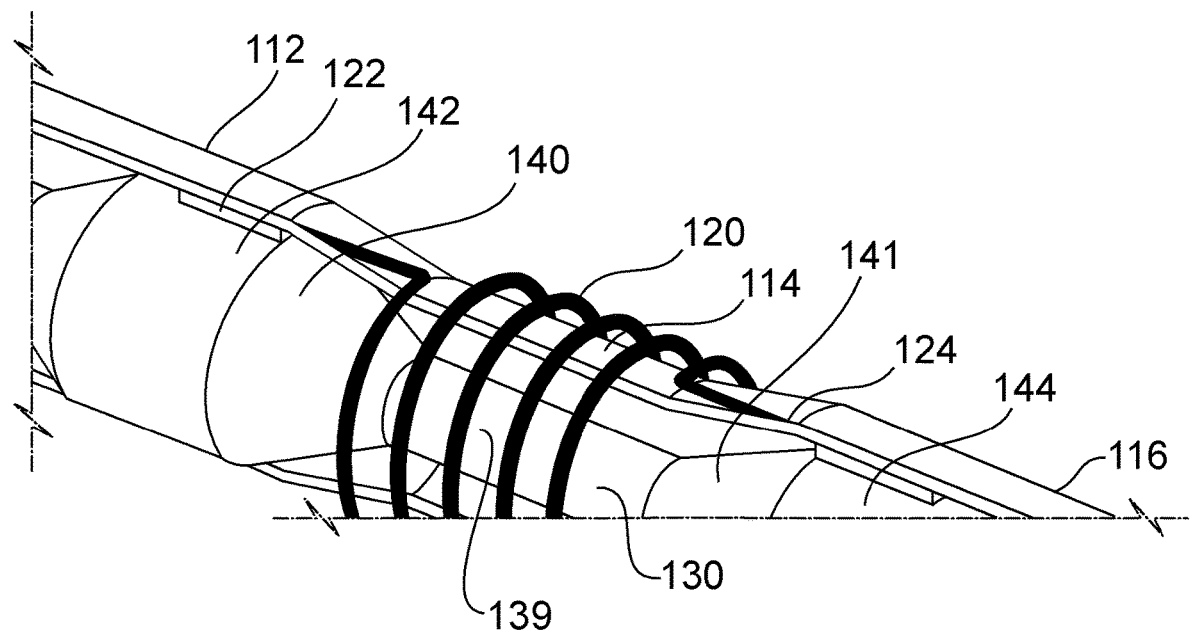
FIG. 3 shows an enlarged view of the TIPS stent graft of FIG. 2 in a use configuration.

Provided so as to surround the central section 114 is a coil 120 made of nitinol. This coil is connected via wires 121 to electrodes 122, 124 which are shown in FIG. 3. By means of those electrodes 122, 124, a current can be led through the coil 120 which will heat up that coil 120. If this heating up heats up the coil 120 beyond its transition temperature, the coil 120 will assume a configuration with a smaller circumference, thereby constricting the central section 114.

FIG. 3 shows in more detail the stent graft 110 shown in FIG. 2 in a configuration where a catheter 130 has been introduced. The catheter 130 has two expanded sections 140 which hold electrodes 142, 144. Those electrodes abut against electrodes 122, 124 of the stent graft. Provided between the expanded sections 140, 141 is a narrower section 139 which is provided inside the central section 114. When applying a voltage to the electrodes 142, 144 of the catheter 130 through wires provided in the inside of the catheter 130 (not shown), a current flows through the wire constituting the coil 120. The coil 120 will then heat up and, if heated above its transition temperature, assume a more constricted configuration, as discussed previously with respect to FIG. 2.

Figure 4:
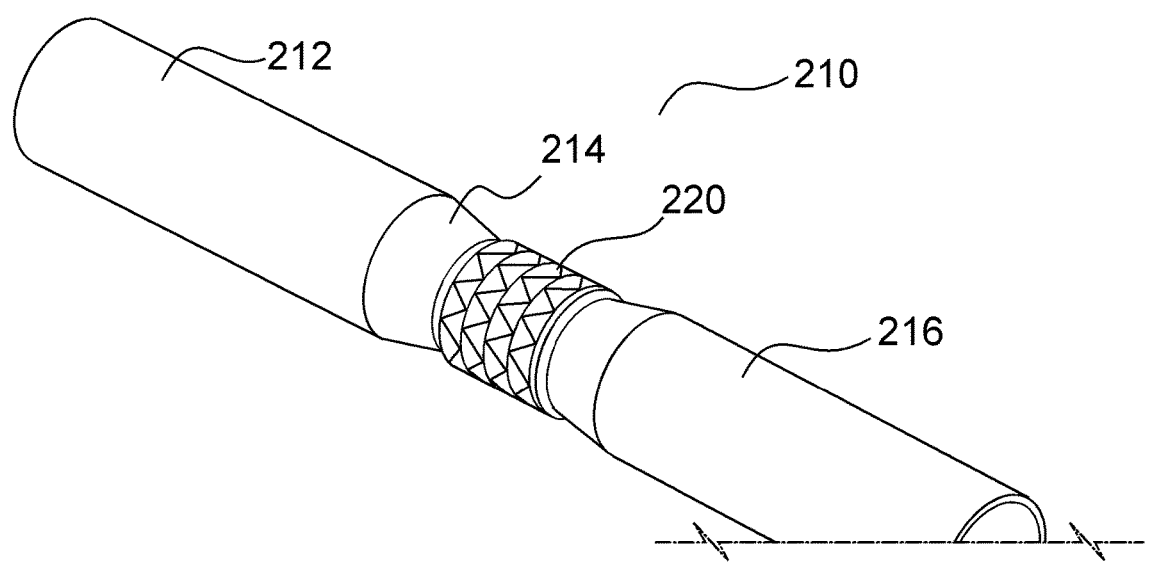
FIG. 4 shows a TIPS stent graft according to a third embodiment.

FIG. 4 shows a third embodiment of the present invention. Between a first self-expanding section 212 and a second self-expanding section 216, a central section 214 with a smaller diameter is arranged. This section is surrounded by a tubular collar 220. This collar is, in turn, connected to electrodes (not shown) provided on the inside of the stent graft 210. When applying a voltage to those electrodes, a current flows through the collar 220 which again causes the collar 220 to heat up and to shrink and to thus assume a constricted configuration. In turn, this reduces the cross-sectional area of the stent graft 210. The further details of the stent graft 210 are identical to what is shown in FIG. 3.

The invention claimed is:

1. A Transjugular Intrahepatic Portosystemic Shunt (TIPS) stent graft, comprising:
   a tubular component having a lumen extending therethrough, the tubular component configured for placement in a liver channel created for a TIPS procedure, the tubular component comprising:
     a diametrically restricted balloon expandable central section;
     a first self-expanding section; and
     a second self-expanding section, the first self-expanding section and the second self-expanding section sandwiching the diametrically restricted balloon expandable central section, the lumen extending through the first self-expanding section, the diametrically restricted balloon expandable central section, and the second self-expanding section, wherein the diametrically restricted balloon expandable central section comprises a shape memory alloy having a transition temperature above body temperature, the diametrically restricted balloon expandable central section being configured to assume a configuration which is more constricted than the first self-expanding section and second self- expanding section in their expanded state when heated above its transition temperature; and
   a collar formed as a cylinder wrapped around the diametrically restricted balloon expandable central section, the collar being arranged to selectively reduce its inner diameter to thereby constrict the diametrically restricted balloon expandable central section.

2. The TIPS stent graft according to claim 1, wherein the collar is arranged to selectively reduce its inner diameter upon an application of heat.

3. The TIPS stent graft according to claim 1, wherein the collar comprises a metal.

4. The TIPS stent graft according to claim 1, the collar being arranged to heat up upon application of electric energy to thus reduce its inner diameter, the TIPS stent graft further comprising electrodes to supply electricity to the collar.

5. The TIPS stent graft according to claim 4, the electrodes being formed on an inside of the TIPS stent graft.

6. The TIPS stent graft according to claim 5, the electrodes comprising a first electrode and a second electrode, with the first electrode being provided on the first self-expanding section and with the second electrode being provided on the second self-expanding section.

7. The TIPS stent graft according to claim 1, wherein the collar comprises a shape memory alloy.

8. The TIPS stent graft according to claim 7, the shape memory alloy having a higher transition temperature than the first section and the second section.

9. The TIPS stent graft according to claim 4, further comprising a catheter comprising electrodes arranged to supply energy to the electrodes of the TIPS stent graft.

* * * * *